United States Patent
Schneider et al.

(10) Patent No.: US 8,061,354 B2
(45) Date of Patent: Nov. 22, 2011

(54) APPARATUS AND METHOD FOR SUPPLYING A RESPIRATORY GAS

(75) Inventors: Hartmut Schneider, Burgeln Marburg (DE); Jörg Meier, Munich (DE); Dieter Heidmann, Berg (DE); Harald Vögele, Gauting (DE); Stefan Madaus, Gräfelfing (DE); Rainer Jakobs, Mannheim (DE); Stefan Schätzl, Weilheim (DE); Richard Brandmeier, Egling (DE)

(73) Assignee: MAP Medizin-Technologie GmbH, Martinsried (DE)

( * ) Notice: Subject to any disclaimer, the term of this patent is extended or adjusted under 35 U.S.C. 154(b) by 111 days.

(21) Appl. No.: 12/750,850

(22) Filed: Mar. 31, 2010

(65) Prior Publication Data

US 2010/0180898 A1    Jul. 22, 2010

Related U.S. Application Data

(63) Continuation of application No. 10/470,348, filed as application No. PCT/EP02/00907 on Jan. 29, 2002, now Pat. No. 7,717,111.

(30) Foreign Application Priority Data

Jan. 29, 2001 (DE) .................................. 101 03 810

(51) Int. Cl.
  *F16K 31/02* (2006.01)
(52) U.S. Cl. ................................. 128/204.23
(58) Field of Classification Search ............ 128/204.18, 128/204.21, 204.23, 205.11
  See application file for complete search history.

(56) References Cited

U.S. PATENT DOCUMENTS

| 5,134,995 A | 8/1992 | Gruenke et al. |
| 5,388,575 A | 2/1995 | Taube |
| 5,546,933 A | 8/1996 | Rapoport et al. |
| 2005/0247315 A1 | 11/2005 | Estes et al. |
| 2006/0011200 A1 | 1/2006 | Remmers et al. |

FOREIGN PATENT DOCUMENTS

| DE | 33 06 607 C2 | 5/1984 |
| DE | 690 21 681 T2 | 5/1991 |
| DE | 692 30 564 T2 | 5/1993 |
| DE | 692 31 157 T2 | 8/1994 |
| DE | 694 25 113 T2 | 6/1995 |
| DE | 100 21 784 A | 11/2000 |
| DE | 102 53 946 B3 | 1/2004 |
| WO | WO 92/11054 A | 7/1992 |
| WO | WO 93/09834 | 5/1993 |

OTHER PUBLICATIONS

German Search Report of Application No. 101 03 810.0, dated May 13, 2003 (4 pages including English Translation).
Germany Examination Report of Application No. 101 03 810.0-44, dated Jun. 16, 2004 (4 pages including English Translation).
International Search Report of Application No. PCT/EP02/00907, dated May 17, 2002 (2 pages).

*Primary Examiner* — Kristen Matter
(74) *Attorney, Agent, or Firm* — Nixon & Vanderhye P.C.

(57) ABSTRACT

An apparatus for supplying a respiratory gas to a patient within the scope of the diagnosis and/or the treatment of sleep-related breathing disorders includes an electronic signal processing device for generating a pressure control signal on the basis of indicative signals relating to the breathing activity and/or the physiological state of a person. The signal processing device includes a signal inputting device and an extraction device for generating data field entries according to predefined signal analysis procedures. A pressure signal generator is provided for generating the pressure control signal, taking into account determined data field entries which are at least selected by the extraction device.

20 Claims, 3 Drawing Sheets

APPARATUS AND METHOD FOR SUPPLYING A RESPIRATORY GAS

CROSS-REFERENCE TO RELATED APPLICATION

This application is a continuation of Ser. No. 10/470,348, filed Jul. 28, 2003, now U.S. Pat. No. 7,717,111, which is the U.S. National Phase of International Application PCT/EP02/00907, filed Jan. 29, 2002, which designated the U.S., and claimed the benefit of DE 10103810, filed Jan. 29, 2001, each incorporated herein by reference in its entirety.

FIELD OF THE INVENTION

The example embodiments disclosed herein relate to an apparatus and method for supplying a respiratory gas to a patient in the context of diagnosis and/or therapy of sleep-related breathing disorders. In particular, the example embodiments disclosed herein relate to a CPAP unit with self-adaptive dual level pressure regulation.

BACKGROUND OF THE INVENTION

Sleep-related breathing disorders, particularly in connection with obstructions in the region of the upper respiratory tracks, can be subjected to therapy in a physiologically well compatible fashion by increased-pressure respiration using a respiratory gas pressure, which is possibly alternating but permanently above the ambient pressure level. This increased-pressure respiration (which is generally referred to as CPAP therapy) is based on "pneumatic splinting" of the upper respiratory tracts, which is achieved by the increased pressure. That pneumatic splinting effect obviates any obstructions in the region of the upper respiratory tracts. In order to ensure that the CPAP therapy enjoys as high a level of physiological compatibility as possible, the endeavor is to reduce the respiration pressure, in particular, during an expiration phase in relation to the inspiration phase.

Hitherto favorable respiration pressure levels can either be selected by the patient himself or, for example, can also be ascertained under the charge of a doctor in the context of a stay on the part of the patient in a sleep laboratory. Investigations have shown however that both the therapy pressures desired by the patient himself and also the therapy pressures ascertained in the course of a stay in a sleep laboratory, for the inspiration pressure and also for the usually somewhat lower expiration pressure, are in part markedly above the inspiration and expiration pressure levels required for the predominant part of the sleep phase.

SUMMARY OF THE INVENTION

Under the impulsion of that problem an aspect of certain example embodiments is to provide an apparatus for supplying a respiratory gas to a patient, by which the respiration pressure level can be still more reliably adapted to the physiological state of the patient.

In accordance with certain example embodiments, that aspect is attained by an apparatus for supplying a respiratory gas comprising an electronic signal processing device for generating a pressure control signal on the basis of signals indicative in respect of the breathing activity and/or physiological state of a person, wherein the signal processing device has a signal input device and an extraction device for generating data field entries in accordance with predetermined signal analysis procedures, and there is provided a pressure signal generator for generating the pressure control signal, wherein the pressure signal generator generates the pressure signal taking into account at least selected data field entries determined on the part of the extraction device.

In that way it is advantageously possible to achieve a respiratory gas supply which is adapted in an improved fashion to the instantaneous physiological demands of the patient.

In accordance with a particularly preferred embodiment of the invention, the extraction device is so designed that evaluation of signals indicative in respect of the respiratory gas flow is effected thereby. Those signals which are indicative in respect of the respiratory gas flow can be generated, for example, by a dynamic pressure detection device or also by measurement circuits on the basis of acoustic principles, including the Doppler effect of an ultrasonic event.

Evaluation of the signals indicative in respect of the respiratory gas flow is preferably effected on the basis of a time series analysis procedure and, in particular, on the basis of variance consideration of the first, second, and third derivatives of the respiratory gas flow.

Preferably, the extraction device is so designed that, in conjunction with evaluation of the respiratory gas flow, it analyzes the deviations of the respiratory gas flow from a reference respiratory flow pattern. That reference respiratory flow pattern can be continuously updated.

It is possible for the extraction device to be so designed that, in conjunction with evaluation of the signals indicative in respect of the respiratory gas flow, a classification data set indicative in respect of the physiological state of the patient is generated. That classification data set can be passed for further evaluation, for example, by a medical specialist, by way of an interface device, for example, by way of an infrared interface or also by way of a portable data carrier.

In accordance with a particularly preferred embodiment of the invention, generated on the part of the extraction device is an interlinking data set which describes a relationship between the data field entries ascertained on the basis of selected analysis criteria. That relationship between the extracted features or the probability of that relationship can be further classified by statistical details so that the significance of the extracted features or the weighting thereof can be suitably taken into account in pressure regulation.

It is possible on the basis of that statistical classification of the extracted features to generate a patient-specific data set which shows, for example, that certain items of information contained in the input signals can be disregarded. Thus, it is possible, for example, on the basis of the patient-specific data set to assess to what degree there is a relationship between the respiration pressure levels and the body position of the patient including, in particular, the degree of turning of the neck or the position of the head. It is possible to statistically describe relationships which occur with a high level of statistical probability or to define them by parameters.

In accordance with a particularly preferred embodiment of the invention, the pressure signal generator is operatively incorporated into the signal processing device in such a way that it takes account of respiration phase data (A) and respiration phase change-over signals (AW) upon generation of the pressure control signal. In that way, it becomes possible to match the configuration in respect of time of the respiratory gas pressure change between the successive respiration phases, in such a way as to ensure a particularly high level of respiration comfort and, in particular, during the phase of dropping off to sleep and with a high blood oxygen content. In accordance with a particularly preferred embodiment of the invention, the respiration phase change-over signals are produced by a respiration phase coordinator which is operatively incorporated into the signal processing device in such a way that, in the same manner as the pressure signal generator, the respiration phase coordinator has access to given field entries of the data field generated by the extraction device.

The respiration phase coordinator is preferably incorporated into the signal processing device in such a way that it also has access substantially in real time to the signals "raw data" at the signal input device or at least signals derived therefrom (for example, filtered in a defined fashion). That makes it possible for respiration phase recognition to be implemented with precise matching to the instantaneous physiological state of the user without in that respect major delay times occurring in terms of analysis of the respiratory gas flow.

In accordance with a particularly preferred embodiment of the invention, respiration phase coordination is effected by respiration phase recognition on the basis of threshold consideration, wherein the threshold value changes with increasing distance in respect of time from the moment in time of the previous respiration phase change. Those change dynamics are adapted in a program-controlled manner preferably on the basis of selected entries in the data field. Respiration phase recognition is preferably also effected with recourse to a more extensive data set including, in particular, a characteristic diagram or mapping, wherein the position within same is ascertained in dependence on the instantaneously recognized physiological state of the user.

The respiration phase coordinator is preferably so designed that in the respiration phase recognition procedure, it analyses the first and preferably also the second derivative of the respiratory gas flow. A particularly high level of reliability in regard to recognition of the individual respiration phases can be achieved if a plurality of recognition criteria are processed in interlinked relationship. It is possible for those recognition criteria to be selected on the basis of fuzzy logic procedures or to be weighted differently in dependence on the data field entries generated by the extraction device.

The respiration phase coordinator and the pressure presetting device are preferably operatively interlinked in such a way that in the case of blurred respiration phase recognition, the distance between the inspiration pressure and the expiration pressure is reduced. It is possible for the pressure presetting device also to be operated with recourse to an additional patient-specific pressure regulation data set. The respiration phase selection data set (6) and the pressure regulation data set can be generated from data fields which are modified with recourse to the data field entries generated on the part of the extraction device.

In accordance with a particularly preferred embodiment of the invention, for finally setting the respiration gas pressure there is provided a pressure adaptation device to which the pressure control signal generated on the part of the pressure presetting device is fed as a reference value. The pressure adaptation device implements automatically and preferably with a high level of regulating dynamics adaptation of the respiration gas pressure, in accordance with the supplied pressure control signal.

In that respect, particularly precise setting of the respiratory gas pressure is achieved by the respiratory gas pressure being detected at a pressure take-off location near the patient. It is possible for the respiratory gas pressure to be set in such a way that only the static pressure component at the pressure take-off location or also the static pressure component in the internal space of a breathing mask corresponds to the respiratory gas pressure which is predetermined in accordance with the pressure control signal. Insofar as direct pressure take-off is not possible in the region of a user, then in accordance with a particularly preferred embodiment of the invention the pressure adaptation device is so designed that it calculates pressure correction values to compensate for conduit-governed pressure drops, having regard to the instantaneous respiratory gas flow.

The apparatus according to certain example embodiments for supplying a respiratory gas is particularly suitable as a CPAP unit with automatically adjusting dual-level pressure regulation.

BRIEF DESCRIPTION OF THE DRAWINGS

Further details and features of the invention are apparent from the description hereinafter of a preferred embodiment by way of example with reference to the drawings, in which.

DETAILED DESCRIPTION OF ILLUSTRATED EMBODIMENTS

Figure 1:
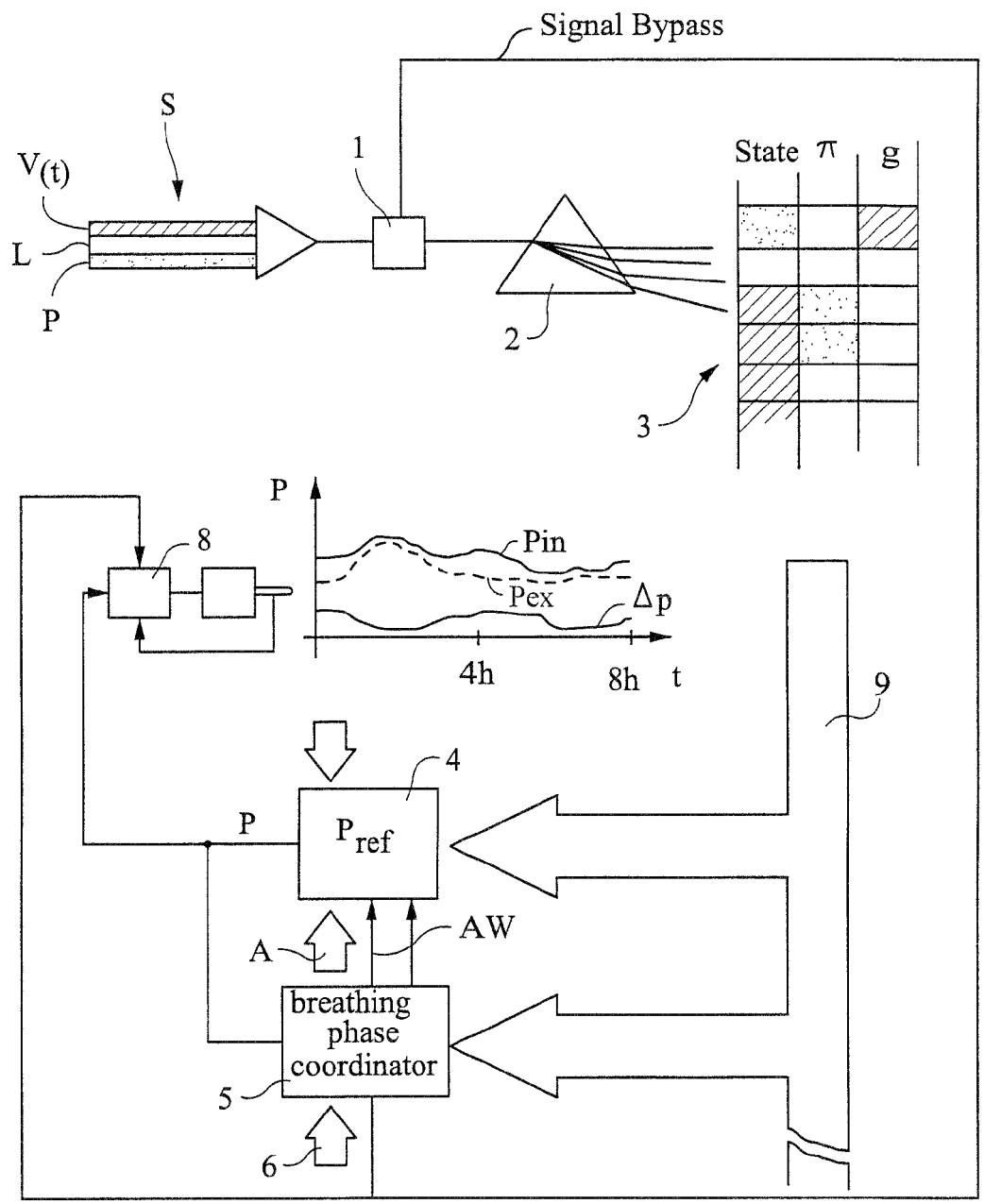
FIG. 1 is a diagrammatic view showing the principle of the regulating concept on which certain example embodiments is based.

In accordance with the regulating concept shown in FIG. 1, signals indicative in respect of the instantaneous physiological state of a patient are supplied to a processing device which is identified hereinafter as the extraction device 2. A data field 3 is filled out in that extraction device 2, on the basis of an adaptive evaluation procedure. The items of information contained in the data field 3 are taken into consideration in regard to adaptation of the instantaneous performance in respect of time of respiratory gas pressure regulation.

In the system illustrated here, a part of the field entries is taken into account when ascertaining a reference inspiration pressure as well as a reference expiration pressure.

The reference pressures are processed in a respiration phase coordinator 5 in conjunction with further entries read out of the criterion field 3. The instantaneous respiratory gas pressure value fixed in that way is supplied to a pressure control device 8 which, in conjunction with a high-dynamic regulating circuit, sets the respiratory gas pressure, for example by controlling a rotary speed of a blower, to the predetermined reference respiratory gas pressure. Setting of the respiratory gas pressures, in extremely close relationship with time, is achieved with the illustrated regulating design insofar as at least a part of the signals S which are taken off at the patient is available to the individual regulating components only filtered by a band pass filter.

The regulating concept according to the invention can be implemented by a sufficiently powerful computer device, in which respect it is possible for the components which here are described in clearly differentiated fashion to be embodied in the form of possibly overlapping subprocedures by a suitable program procedure.

In the extraction device 2 preferably at least one signal (V(t)) indicative in respect of the instantaneous respiratory gas flow is subjected to a time series analysis procedure, in which respect preferably at least the first, second, and third derivatives of that signal are formed. In addition statistical parameters, in particular the variance of the signal configuration, or the time derivatives thereof, are ascertained. The features ascertained in connection with the individual curve discussion criteria are entered in the field 3 preferably in connection with a statistical certainty and a weighting factor possibly changing with increasing statistical expressiveness or interlinking parameters. At least a part of the details entered in the field 3 is taken into account when adapting the performance in respect of time of actual respiratory gas pressure regulation.

In the embodiment illustrated here, besides signals indicative in respect of the respiratory gas flow, position signals (L), and signals indicative in respect of the respiratory gas pressure are also detected by way of the signal input device 1. Those signals are available in a defined, filtered form if required for the regulating systems of the signal processing device according to certain example embodiments of the invention. In the embodiment illustrated here, a multi-dimensional data field 3 is generated by the extraction device 2. Disposed in that data field 3 are the dynamically changing data field entries generated by the extraction device. In the illustrated embodiment further items of information, in particular details relating to the statistical certainty, are associated with given data field entries generated by the extraction device 2. The data field entries stored in the data field 3, which is dynamically managed in accordance with the extraction device 2, are available to the pressure presetting device 4 and the respiration phase coordinator 5, as indicated by data flow arrows 9.

The pressure presetting device 4 ascertains, for example, on the basis of selected data field entries in the dynamic data field 3 the maximum inspiration pressure and the maximum expiration pressure. In addition the data presetting device 4 ascertains a pressure configuration in respect of time, which is adapted to the instantaneous physiological state of the spontaneously breathing person, at the change between the two respiration phases.

Recognition or identification of the respiration phases is effected by way of the respiration phase coordinator 5, which also has access to selected data field entries in the data field 3. The respiration phase coordinator 5 is further in a nearly dead time-free signal relationship with the signal input device 1. Assessment of the breathing activity of the spontaneously breathing person by the respiration phase coordinator 5 is additionally effected in the illustrated embodiment having regard to patient-specific presetting parameters and also having regard to the pressure control signals P which are predetermined on the part of the pressure presetting device 4.

It is possible in that way, in respiratory gas supply periods with comparatively large differences between the inspiration respiratory gas pressure and the expiration respiratory gas pressure, to implement respiration phase recognition with a higher level of sensitivity, whereas when there are comparatively small differences between the respiratory gas inspiration pressure and the respiratory gas expiration pressure, other criteria can be used to form the basis for recognition of or determination of the respiration phases.

The pressure control signals P which are generated on the part of the pressure presetting device 4 are supplied to a pressure adaptation device 8 for actuation of the members relevant for building up the respiratory gas pressure, for example a blower device. Regulation of the respiratory gas pressure in accordance with the pressure control signal P can be affected by way of a high-dynamic regulating circuit provided for that purpose, which has its own pressure detection members.

In conjunction with the described signal processing device according to certain example embodiments of the invention, it is now possible to guarantee a stable and precise setting of the respiratory gas pressure, which is adapted to the physiological requirements of a spontaneously breathing person.

As can be seen from the diagram incorporated into the view in FIG. 1 the mean inspiration pressure (Pin) and the mean expiration pressure (Pex) of a respiration phase vary in the course of a period of time extending over the sleep phase of a patient. In dependence on given parameters which are indicative in respect of the physiological state (I, II, III) of the spontaneously breathing person, in that situation there are pressure distances ($\Delta p$) of different magnitudes between the mean inspiration pressure (Pin) and the mean expiration pressure (Pex) of each breath. Recognition of the respiration phases by the respiration phase selector 5 is also adapted in dependence on that pressure difference.

Adaptation both of the inspiration pressure and also the expiration pressure can be effected on the basis of a patient-specifically adapted characteristic diagram or mapping, in which case the instantaneous position in that diagram can be implemented on the basis of classification details which are ascertained in conjunction with the data field entries 3 generated by the extraction device 2.

Figure 2:
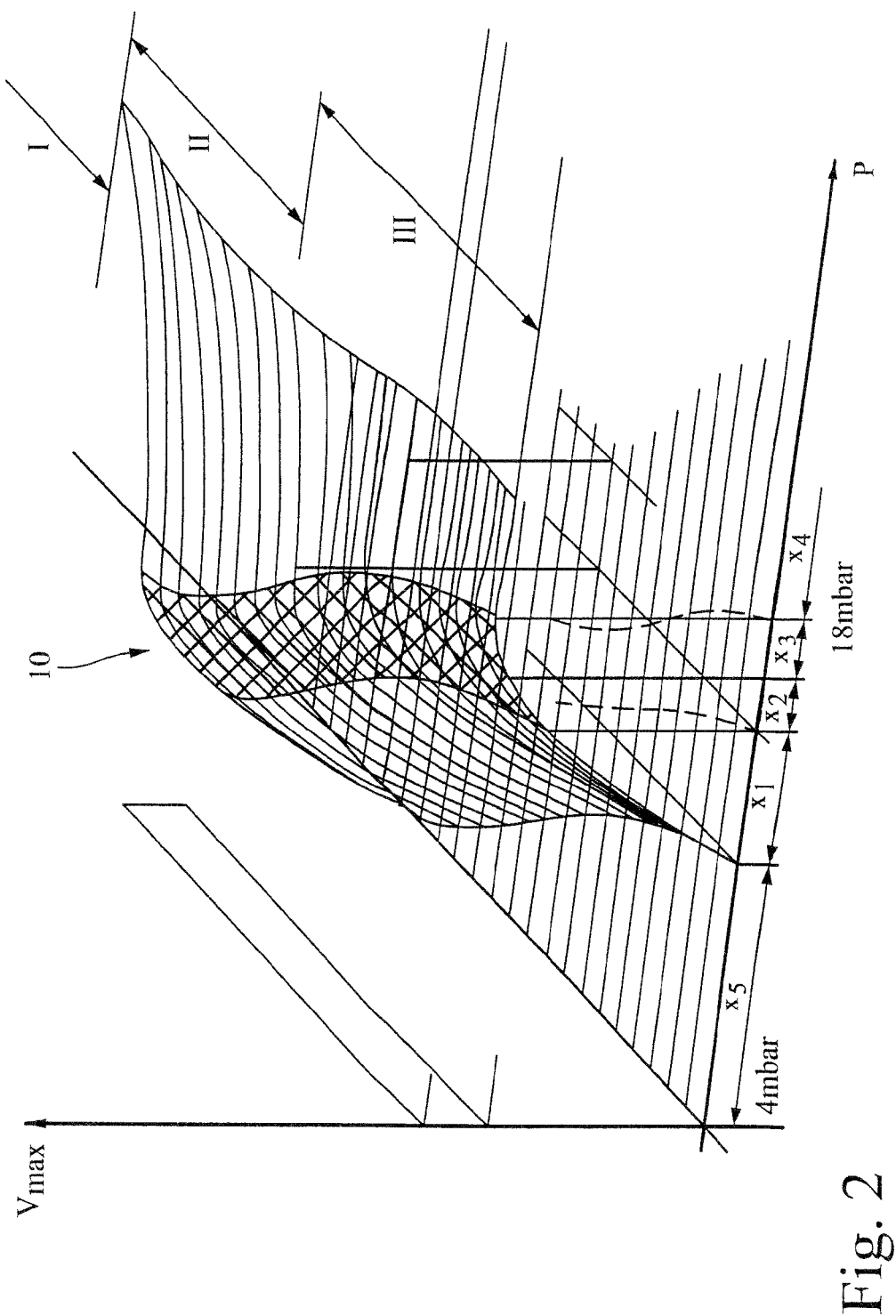
FIG. 2 is a multi-dimensional characteristic diagram or mapping which is adapted in patient-specific fashion and which represents the relationship between the respiratory gas pressure and the maximum respiratory gas flow (Vmax) that entails, for different physiological states (I, II, III) of the patient.

In the embodiment illustrated in FIG. 2, the data field entries present in the dynamic data field 3 are used to ascertain which region of the characteristic diagram illustrated here is to be utilized for instantaneous regulation of the respiratory gas pressure. A maximum respiratory gas inspiration pressure and in association therewith a minimum respiratory gas expiration pressure is ascertained on the basis of a selection made in that way in respect of the patient-specifically adapted characteristic diagram region. Those two pressure levels preferably lie within the bend region 10 of the characteristic diagram, which is here indicated by heavier hatching. In the present embodiment the characteristic diagram extends over a CPAP pressure region of 4-18 mb. The distance ($\times 1$, $\times 2$, $\times 3$, $\times 4$, $\times 5$) between the maximum inspiration pressure and the minimum expiration pressure is below 6 mb in the patient-specific characteristic diagram illustrated here. Besides the gradient of the characteristic diagram in the illustrated bend region 10 the distance between the maximum inspiration pressure and the minimum expiration pressure is also determined by further influencing factors which are ascertained on the basis of the data field dynamically filled in by the extraction device 2.

Figure 3:
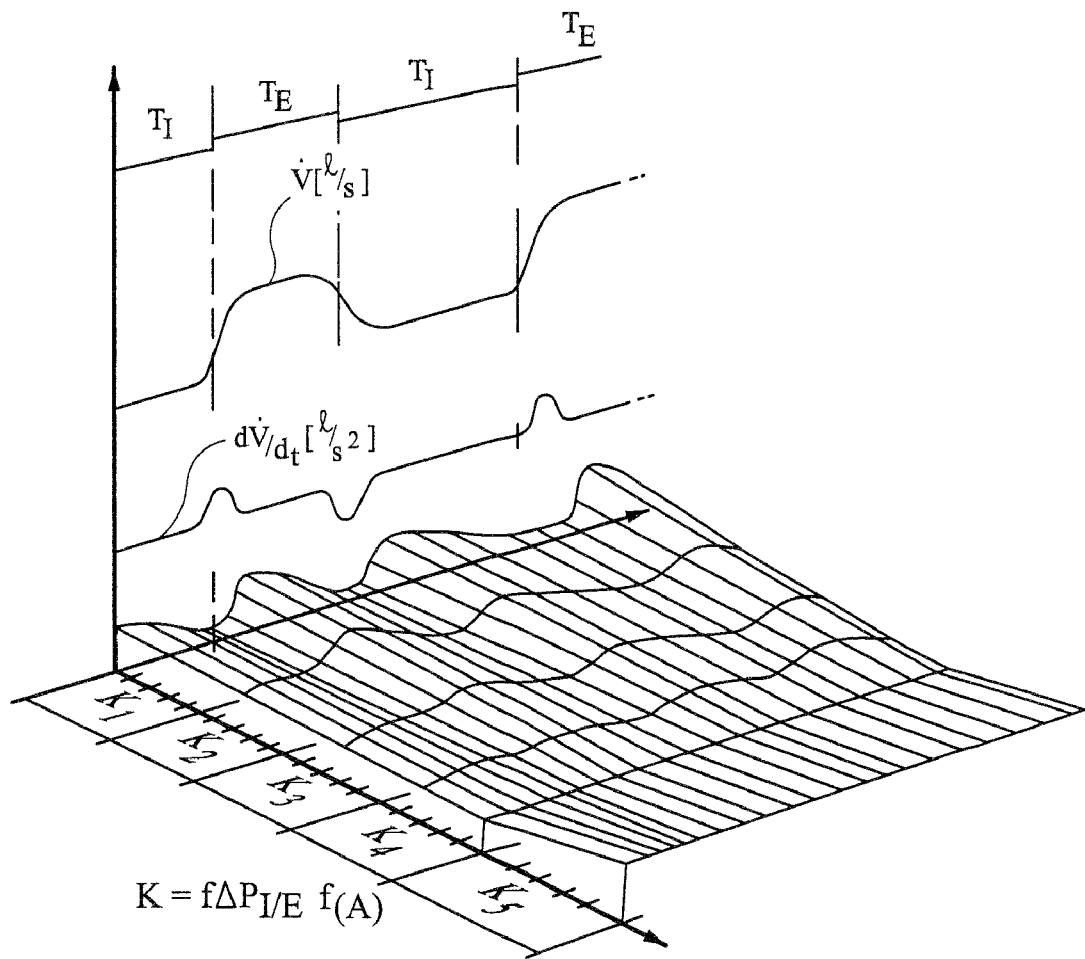
FIG. 3 shows a diagram to explain the assessment criteria which are continuously adapted in dependence on a criterion grid for detection of the respiration cycles of a patient and for adaptation of pressure change-over.

The view in FIG. 3 shows in qualitative terms the configuration in respect of time of the respiratory gas flow V, with association of the inspiration phases $T_I$ and expiration phases $T_E$ recognized on the part of the respiration phase coordinator 5. Diagrammatically illustrated below the respiratory gas flow curve is the first derivative thereof. In dependence on the entries in the data field 3 and preferably also in dependence on the pressure control signal P predetermined on the part of the pressure presetting device 4, the criteria for respiration phase recognition are adapted. In the embodiment illustrated here, in a first respiration phase classification category $K_1$ respiration phase recognition is affected by threshold value comparison with a threshold value which changes in respect of time with a high level of dynamics from a comparatively large value to a relatively low value. The threshold value is increased again immediately after recognition of a change in respiration phase. Immediate switching back into the preceding respiration phase is avoided by virtue of a dynamically adapted dead time. In the classification category $K_2$ the deviation between the maximum threshold value and the minimum threshold value is already less. Even smaller is the difference between the two threshold values in the classification category $K_3$. In the classification category $K_4$ respiration phase recognition is affected on the basis of an almost constant threshold value. In the classification category $K_5$ respiration phase recognition is also affected on the basis of constant threshold values which however increase in dependence on the data field entries.

The classification categories are preferably implemented in dependence on a respiration pattern recognition procedure which is implemented by the extraction device 2 and communicated by data field entries.

The apparatus according to certain example embodiments of the invention makes it possible to provide a CPAP unit for carrying out respiration therapy in the domestic area, which automatically adapts the respiratory gas pressure both for the inspiration process and also for the expiration process to the physiological requirements of a user.

The extraction device provided in accordance with the invention makes it possible to classify the instantaneous physiological state of the user by detection of breathing activity. On the basis of that classification, it is then possible to establish the instantaneously most favorable respiratory gas pressure values for the inspiration process and for the expiration process. In addition it is now possible to implement respiration phase recognition which is required for setting the possibly differing pressure levels, with a high level of precision.

What is claimed is:

1. An apparatus for supplying a respiratory gas to a patient, comprising:
   a signal input device configured to receive signals indicative of an instantaneous respiratory gas flow, a position of the patient, and a respiratory gas pressure;
   a processing device configured to dynamically generate entries of a multi-dimensional data field in accordance with predetermined signal analysis procedures, the entries defining a relationship between the respiratory gas pressure and a maximum respiratory gas flow for a plurality of different physiological states of the patient;
   a pressure presetting device configured to dynamically determine, on the basis of selected data field entries of the multi-dimensional data field, a maximum inspiration phase pressure, a maximum expiration phase pressure, and a pressure adapted to the instantaneous physiological state of the patient at a change between the respiration phases, the pressure presetting device being further configured to dynamically generate a pressure control signal indicative of the pressure adapted to the instantaneous physiological state of the patient at the change between the respiration phases;
   a respiration phase coordinating device configured to dynamically identify, on the basis of selected data field entries of the multi-dimensional data field and on the basis of the dynamic pressure control signal generated by the pressure presetting device, a respiration phase of the patient; and
   a pressure control device configured to receive the dynamic pressure control signal generated by the pressure presetting device and dynamically control the respiratory gas pressure to the pressure adapted to the instantaneous physiological state of the patient at a change between respiration phases.

2. An apparatus according to claim 1, further comprising a signal bypass configured to bypass the signals indicative of the instantaneous respiratory gas flow, the position of the patient, and the respiratory gas pressure directly to the respiration phase coordinating device and/or the pressure control device.

3. An apparatus according to claim 2, further comprising a filter configured to filter the bypassed signals.

4. An apparatus according to claim 3, wherein the filter comprises a band pass filter.

5. An apparatus according to claim 1, wherein the processing device is further configured to generate, based on a statistical classification of the entries of the multi-dimensional data field, a patient-specific data set that defines a relationship between the respiratory gas pressure and a physiological state of the patient.

6. An apparatus according to claim 5, wherein the patient-specific data set defines a relationship between the respiratory gas pressure and a body position of the patient.

7. An apparatus according to claim 6, wherein the body position of the patient comprises a degree of turning of the neck of the patient.

8. An apparatus according to claim 5, wherein the respiration phase coordinating device is configured to identify the respiration phase in dependence on a difference between a mean inspiration pressure and a mean expiration pressure over a period of time and a physiological state of the patient.

9. An apparatus according to claim 8, wherein the patient-specific data set comprises a maximum inspiration pressure and a minimum expiration pressure of the patient.

10. An apparatus according to claim 9, wherein the maximum inspiration pressure and the minimum expiration pressure are between a range of about 4-18 millibar.

11. An apparatus according to claim 8, wherein the respiration phase coordinating device is configured to identify the respiration phase in dependence on a first derivative of the respiratory gas flow.

12. An apparatus according to claim 11, wherein the respiration phase coordinating device is configured to identify the respiration phase in dependence on a second derivative of the respiratory gas flow.

13. An apparatus according to claim 1, wherein the signals indicative of the instantaneous respiratory gas flow are generated by a dynamic pressure detection device.

14. An apparatus according to claim 1, wherein the signals indicative of the instantaneous respiratory gas flow are generated by a measurement circuit configured to detect a Doppler effect of an ultrasonic event.

15. An apparatus according to claim 1, wherein the respiration phase coordinating device is in a substantially dead time-free signal relationship with the signal input device.

16. An apparatus according to claim 1, wherein the instantaneous physiological state of the patient comprises at least one instantaneous physiological demand of the patient.

17. An apparatus according to claim 16, wherein the at least one physiological demand of the patient comprises an increased blood oxygen content during a phase of dropping off to sleep.

18. A CPAP apparatus, comprising:
   a blower configured to generate a flow of pressurized breathable gas; and
   an apparatus according to claim 1.

19. A CPAP apparatus according to claim 18, wherein the pressure control signal is configured to control a rotary speed of the blower.

20. A method of supplying a respiratory gas to a patient, comprising:
   receiving signals indicative of an instantaneous respiratory gas flow, a position of the patient, and a respiratory gas pressure;

dynamically generating entries of a multi-dimensional data field in accordance with predetermined signal analysis procedures, the entries defining a relationship between the respiratory gas pressure and a maximum respiratory gas flow for a plurality of different physiological states of the patient;

dynamically determining, on the basis of selected data field entries of the multi-dimensional data field, a maximum inspiration phase pressure, a maximum expiration phase pressure, and a pressure adapted to the instantaneous physiological state of the patient at a change between the respiration phases;

dynamically generating a pressure control signal indicative of the pressure adapted to the instantaneous physiological state of the patient at the change between the respiration phases;

dynamically identifying, on the basis of selected data field entries of the multi-dimensional data field and on the basis of the dynamic pressure control signal, a respiration phase of the patient; and dynamically controlling the respiratory gas pressure to the pressure adapted to the instantaneous physiological state of the patient at the change between the respiration phases on the basis of the pressure control signal.

* * * * *